United States Patent [19]

Willis

[11] Patent Number: 5,625,666

[45] Date of Patent: Apr. 29, 1997

[54] RADIOGRAPHIC FILM RETAINING DEVICE

[76] Inventor: Timothy G. Willis, 310 Evergreen, Yreka, Calif. 96097

[21] Appl. No.: 563,992

[22] Filed: Nov. 29, 1995

[51] Int. Cl.⁶ ................................................. G03B 42/02
[52] U.S. Cl. .......................... 378/167; 378/170; 378/187; 378/168
[58] Field of Search ..................... 378/167, 168, 378/170, 175, 187, 205

[56] References Cited

U.S. PATENT DOCUMENTS

| | | | |
|---|---|---|---|
| 3,003,062 | 10/1961 | Updegrave | 250/70 |
| 3,864,576 | 2/1975 | Stevenson | 250/505 |
| 5,044,009 | 8/1991 | Klauser | 378/170 |
| 5,256,982 | 10/1993 | Willis | 370/170 |
| 5,289,522 | 2/1994 | Kanbar et al. | 378/170 |
| 5,473,662 | 12/1995 | Barish | 378/170 |

FOREIGN PATENT DOCUMENTS 0397599  5/1990  European Pat. Off. .

OTHER PUBLICATIONS

Dunvale Endex Instruments, date unknown.
Hawe, Periapical radiographs, date unknown.
Dunvale, Champ Instruments, date unknown.
Rinn, Intraoral Radiography, date unknown.

*Primary Examiner*—Don Wong
*Attorney, Agent, or Firm*—Julian Caplan, Esq.; Flehr, Hohbach, Test, Albritton & Herbert

[57] ABSTRACT

A radiographic film retaining device for holding a film packet while producing a radiographic image of selected teeth of a patient's mouth is disclosed. The retaining device includes a substantially thin bite portion configured for placement between upper and lower teeth of the patient's mouth and a retaining structure positioned distally of the bite portion. The retaining structure has a film packet gripping structure for holding the film packet lingually adjacent the selected teeth when the bite portion is gripped between the upper and lower teeth. The retaining structure comprises a narrow extension of the bite portion. The film packet gripping structure includes a slit formed and extending through the retaining structure from the distal end thereof toward the bite portion. The device also has means for locating an x-ray machine cone in proper position relative to the film packet.

6 Claims, 2 Drawing Sheets

RADIOGRAPHIC FILM RETAINING DEVICE

CROSS REFERENCE TO RELATED APPLICATIONS

This invention is an improvement upon my U.S. Pat. No. 5,256,982, issued Oct. 26, 1993.

1. Field of the Invention

This invention relates in general to a radiographic film holder particularly useful in general dentistry. More particularly, the present invention relates to a retaining device for holding a film packet while producing a radiographic image of selected teeth of a patient's mouth.

2. Prior Art

Radiographic film holders suitable for general dentistry are well known in the art. The film holder traditionally includes a bite tab and is formed for receiving a piece of radiographic film. To properly position the holder within the patient's mouth, the upper and lower teeth grip the bite tab.

One type of film holder commonly used in the dental industry is a film packet having an integral bite tab. A piece of radiographic film is enclosed within the film packet, generally formed of cardboard. The tab is positioned at the midpoint of the film packet. To prepare an x-ray of selected teeth, the upper and lower edges of the film packet are slightly bent in a direction opposite the tab. A dental assistant inserts the holder into the mouth, and the patient bites down on the tab while a radiographic image is produced. After removal from the patient's mouth, the radiographic film is retrieved and the film packet is thrown away.

This type of film holder may conveniently be used while producing a radiographic image of selected teeth. When using bitewing film, a dental x-ray film designed to simultaneously photograph the crowns of the upper and lower teeth, the film must be held level within the patient's mouth to provide the dentist with a complete image of the patient's teeth. If a patient is missing teeth, or if the teeth are uneven or hypererupted, the patient will not bite down evenly on the tab, producing an incomplete image. In addition, the film holder may only be used once. This places a significant strain on environmental resources. A film retaining device which will hold a piece of radiographic film level relative to selected teeth of a patient's mouth is desirable. Similarly, a retaining device which may be repeatedly used would be particularly useful for preserving the environment.

Another variety of film holders available in the dental industry includes a bite tab having a depression or hole formed for receiving long or uneven teeth. The film holder may be used to produce complete images of the upper and lower teeth of a patient's mouth. However, in many instances the uneven or hypererupted teeth will not be completely accommodated within the depression or hole of the bite tab. The radiographic film will not be held level within the patient's mouth and the resulting image will be incomplete. A film retaining device which effectively holds the radiographic film level within the patient's mouth is desirable.

To provide a film holder which may be reused, a number of film holders include a groove formed to receive a packet of radiographic film. The patient grips a bite tab between his upper and lower teeth to position the holder within the mouth while producing an image of selected teeth. The location and orientation of the film retaining groove relative to the bite tab determines which of the patient's teeth will be photographed. A film holder having only one groove is not suitable for alternatively producing an image of the crowns of opposed teeth or an image of an entire tooth including the roots. The dentist must maintain a supply of several different film holders each suitable for producing one of several desired images. A film retaining device suitable for holding a piece of radiographic film in several different positions of orientation relative to the film holder is desirable.

Other film holders include more than one groove for holding the film packet in different positions. While providing increased versatility as to the orientation of the radiographic film relative to selected teeth, the film holder will not accommodate variations within a patient's mouth structure. If the patient has uneven or hypererupted teeth, the radiographic film may not be properly oriented adjacent the selected teeth. The resulting image would not depict the entire tooth structure needed. Additional radiographic images would have to be prepared, at the inconvenience of both the dentist and the patient. A film retaining device which will retain a film packet in a plurality of positions of orientation to adjust the position of the film packet relative to selected teeth of a patient's mouth is desirable.

A feature of this invention which distinguishes it over U.S. Pat. No. 5,256,982 is an arm in the plane of the film holder extending substantially perpendicular to the handle thereof which is provided at its outer end with a semicircular locator properly located relative to the film packet held in the device so that the tip of a dental x-ray machine resting in the locator is properly aligned with the film packet.

Accordingly, a primary object of the present invention is to provide a radiographic film retaining device for holding a film packet while producing a radiographic image of selected teeth in a patient's mouth.

A further object of the present invention is to provide a radiographic film retaining device which holds a film packet level within the patient's mouth.

Another object of the present invention is to provide a radiographic film retaining device suitable for holding a film packet in a plurality of positions of orientation for adjusting the position of the film packet relative to selected teeth of the patient's mouth.

An additional object of the present invention is to provide a radiographic film retaining device suitable for holding a film packet having one of a plurality of different sizes.

Yet another object of the present invention is to provide a radiographic film retaining device which may be reused for holding a film packet while producing a radiographic image of selected teeth.

Another object of this invention is the convenient, rapid alignment of the dental x-ray tip with the film packet, thereby reducing the time required to x-ray a film and reducing the chance of misalignment.

A more general object of the present invention is to provide a radiographic film retaining device which may be comfortably inserted into and held within the patient's mouth, which does not inflict pain while the radiographic image is produced, and which may be efficiently and inexpensively manufactured.

SUMMARY OF THE INVENTION

The radiographic film retaining device of the present invention is particularly suitable for holding a film packet and properly locating an x-ray machine while producing a radiographic image of selected teeth of a patient's mouth. The retaining device includes a substantially thin bite portion which is configured for placement between the upper and lower teeth of the patient's mouth. A retaining structure positioned distally of the bite portion includes a film packet gripping structure for retaining a portion of the film packet. When the patient bites down on the bite portion, gripping it between his upper and lower teeth, the retaining structure holds the film packet lingually adjacent the selected teeth.

The retaining structure comprises a narrow extension of the bite portion. The film packet gripping structure includes a slit formed in the retaining structure. The slit extends through the retaining structure from the distal end of the retaining structure towards the bite portion.

In the preferred embodiment, the film packet gripping structure is offset relative to the longitudinal axis of the bite portion. The film packet gripping structure and the bite portion define a recessed area shaped to receive the selected teeth. The slit is located and dimensioned to hold the film packet in a plurality of positions of orientation relative to the retaining structure. In another aspect of the present invention, the slit is formed to retain a film packet having one of a plurality of different sizes.

A conventional dental x-ray machine has a tip from which the x-rays are emitted. Such a tip is usually cylindrical. The present invention has an arm extending in the plane of the holder and generally perpendicular to the film packet as well as the handle of the holder. A semicircular locator extends perpendicular to the arm adjacent the outer end thereof. The tip of the machine fits into the locator and thus the x-rays are directed toward the film pocket. This improvement facilitates location of the machine.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE PREFERRED EMBODIMENTS

Figure 1:
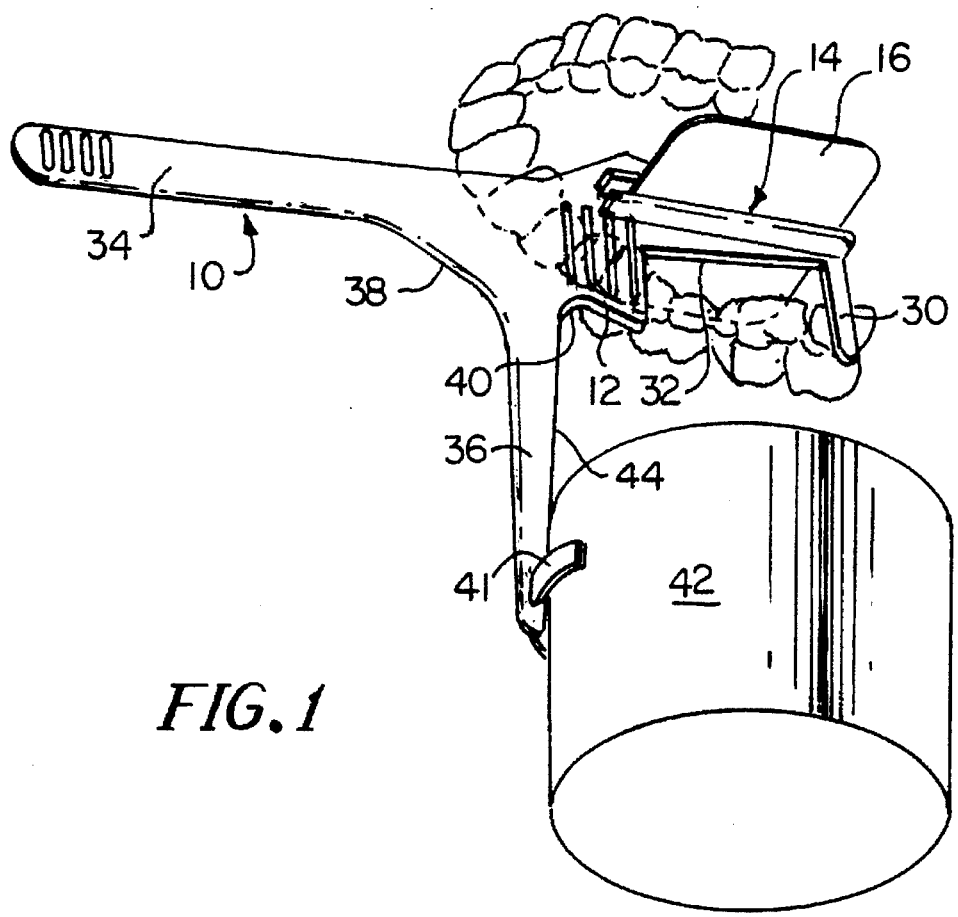
FIG. 1 is an isometric view of a radiographic film retaining device constructed in accordance with the present invention, shown holding a film packet and an x-ray machine tip.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

The preferred embodiment of a radiographic film retaining device constructed in accordance with the present invention is illustrated in FIGS. 1-6. Radiographic film retaining device 10 includes a substantially thin bite portion 12 and a retaining structure 14 positioned distally of the bite portion for holding a film packet 16. The bite portion is configured for placement between the upper and lower teeth. A number of ridges 18 protrude from the surface of the bite portion, improving the grip of the patient's teeth on the retaining device.

When producing an x-ray or radiographic image of selected teeth of the patient's mouth, the patient grips the bite portion between his upper and lower teeth. The retaining structure holds the film packet lingually adjacent selected teeth while a radiographic image is produced. Retaining structure 14, positioned distally of bite portion 12, comprises a narrow extension of the bite portion. The retaining structure includes a film packet gripping structure or gripping members 20 extending through the retaining structure from distal end 22 toward the bite portion for holding the film packet. In the preferred embodiment, gripping structure 20 includes a substantially narrow slit 24 for retaining the film packet. The slit extends through the retaining structure from the distal end to bite portion 12.

Figure 2:
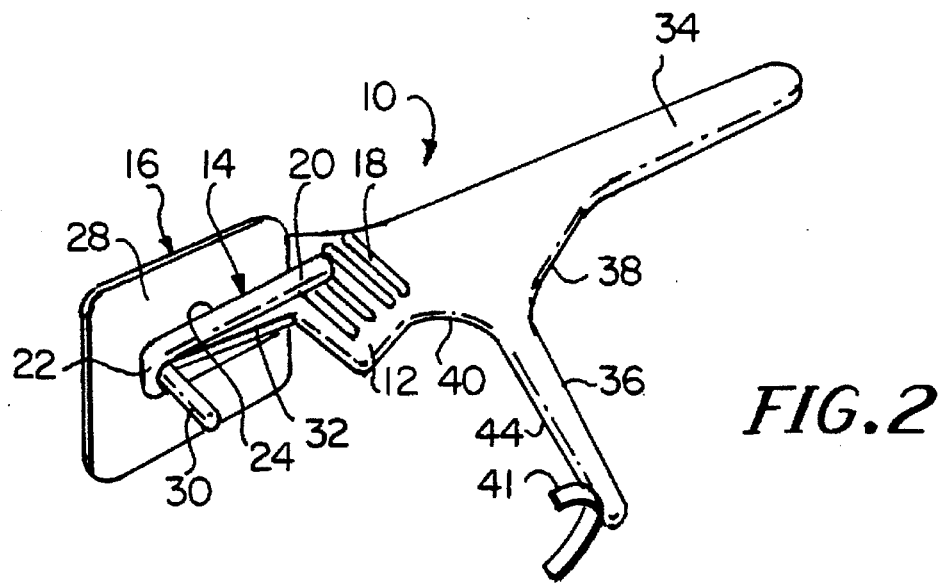
FIG. 2 is an isometric view of the radiographic film retaining device of FIG. 1.
Figure 3:
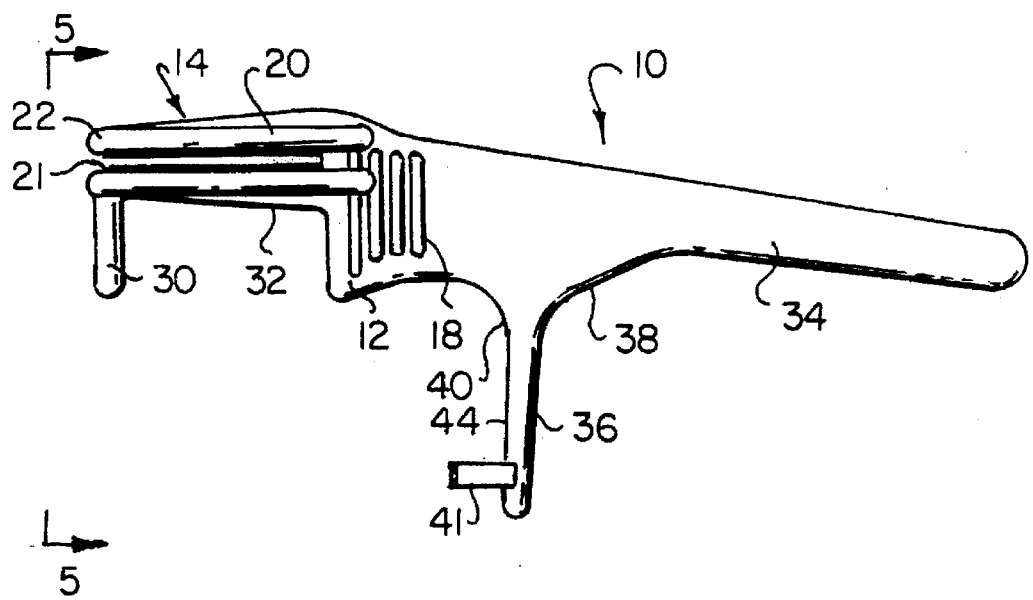
FIG. 3 is a top plan view of the radiographic film retaining device of FIG. 1.
Figure 4:
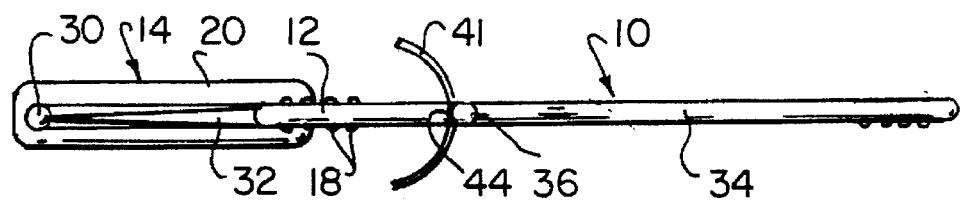
FIG. 4 is a side elevational view of the radiographic film retaining device of FIG. 1.
Figure 5:
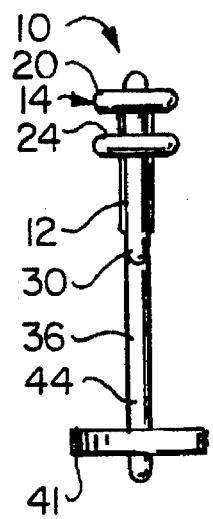
FIG. 5 is an enlarged end elevational view of the radiographic film retaining device taken along line 5—5 of FIG. 3.

Film packet 16 is retained within slit 24 in a plane substantially transverse to the bite portion. When the patient grips the bite portion between his upper and lower teeth, the film packet is held lingually adjacent selected teeth. The slit is located and dimensioned to hold the film packet in one of several positions of orientation. Turning specifically to FIG. 1, the film packet is held in a first position suitable for photographing a substantial portion of opposed upper and lower teeth. In FIG. 2, the film packet is retained in a second position for producing an image of the crowns of several upper and lower teeth. The two orientations of film packet 16 are shown by way of example. The film packet may be held in several alternative positions of orientation. For example, instead of gripping the middle of the film packet, the gripping structure may engage lower edge 26 while producing an image of an upper tooth. Thus, the retaining device will accommodate any dental condition, including missing teeth and gum disease. Similarly, slit 24 is suitable for holding a film packet having one of several different sizes. For example, the retaining device of the present invention may be used in the mouth of a child or an adult.

One type of film packet used in the dental industry consists of a substantially rectangular piece of radiographic film (not shown) enclosed within a polymeric protective envelope 28. The film packet is flexible, and will yield to conform to the contour of the patient's mouth. The film packet is available in several sizes appropriate for different mouth capacities and dental conditions.

In the preferred form of the present invention, a substantially thin second bite portion 30 projects from the retaining structure transverse to gripping structure 20. In the preferred form shown in the drawings, second bite portion 30 is rectangular in cross-section, having flat top and bottom surfaces readily gripped between the patient's teeth. The second bite portion ensures that the film packet is maintained in a level orientation relative to the teeth. When the retaining device is inserted within the patient's mouth, bite potion 30 rests against the back teeth. Bite portion 12 is gripped between upper and lower teeth which are located toward the front of the mouth to hold the retaining device in position. When a patient is missing one of the molars, the film packet is properly aligned as the patient grips bite potion 12. If the patient suffers from a dental condition preventing the upper and lower teeth from properly gripping bite portion 12, the second bite portion 30 will balance the retaining device within the patient's mouth.

When preparing a bitewing image, a depiction of the crowns of the upper and lower teeth, the radiographic film must be held level within the patient's mouth. To properly position the film packet adjacent selected teeth, gripping structure 20 is offset relative to the longitudinal axis of the bite portion. Film retaining device 10 of the present invention includes a recess or recessed area 32 shaped to receive the selected teeth. The recess is defined by bite portion 30, gripping structure 20 and bite portion 12. When the retaining device is inserted into the patient's mouth, the upper and lower teeth grip bite portion 12 while the selected teeth are substantially received within recessed area 32.

The selected teeth do not contact the bite portion, but are instead disposed within the recessed area. With the recessed area of the present invention, the interengagement between the upper and lower selected teeth will be depicted in the radiographic image. Uneven or hypererupted teeth will not distort the positioning of the film since the selected teeth do not contact the bite portion. Thus, the retaining device is properly positioned within the mouth with the radiographic film properly aligned relative to the selected teeth.

Handle portion 34 is integrally formed with bite portion 12 to facilitate the manipulation of the retaining device into and out of the patient's mouth. When preparing to produce a radiographic image of selected teeth, the dentist will grasp the handle portion and carefully position the retaining structure within the patient's mouth. The dentist's fingers will not enter the patient's mouth, vastly improving the patient's comfort. The substantially thin handle portion will not obstruct the dentist's view of the patient's mouth, allowing retaining structure 14 to be more precisely positioned adjacent the selected teeth.

An integral arm 36 in the plane of the handle 34 extends perpendicular thereto in a direction away from the patient's teeth. Curved edges 38, 40 reinforce the arm 36. Adjacent the outer end of arm 36 is a semicircular locator 41.

Tip 42 of an x-ray machine is usually cylindrical. By placing tip 42 within locator 41 and abutting inner edge 44 of arm 36, the x-rays are directed at film packet 16.

The retaining device of the present invention is preferably formed of a polymeric material, such as nylon. The polymeric material provides a retaining device which may be repeatedly sterilized and reused. However, other materials may be substituted. Since the gripping structure is shaped to retain the film packet in several different positions of orientation, a single film retaining device may be used for numerous applications. Thus, the dentist need not maintain a supply of several different types of film holding devices. The film packet may be easily placed within the gripping structure slit and adjusted to a desired location, improving the efficiency of producing radiographic images and reducing patient discomfort.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. An integral, rigid radiographic film retaining device for holding a film packet for use with x-ray equipment having a cylindrical tip while producing a radiographic image of selected teeth of a patient's mouth, said film packet comprising a substantially rectangular piece of radiographic film enclosed within a protective envelope, said retaining device comprising:

(a) a bite portion configured for placement between upper and lower teeth of a patient's mouth;

(b) retaining means positioned distally of said bite portion having a U-shaped film packet gripping means for retaining a portion of said film packet such that when said bite portion is gripped between said upper and lower teeth, said retaining means holds said film packet lingually adjacent said selected teeth, said retaining means comprising a distal extension of said bite portion; and (c) an integral arm extending outwardly of the patient's mouth perpendicular to said film packet and an arcuate x-ray machine tip locator on said arm shaped complementary to said cylindrical tip to engage said tip to direct x-rays toward said film packet, said bite location, said retaining means and said arm being substantially co-planar, said arm having an edge against which said tip may be positioned, said arm and said tip locator cooperating to locate said tip perpendicular to said film packet.

2. The retaining device of claim 1 wherein said bite portion has a longitudinal axis and said film packet gripping means is offset relative to said longitudinal axis, said film packet gripping means and said bite portion defining a substantially rectangular recessed area shaped to receive said selected teeth.

3. A retaining device according to claim 1 in which said film packeting gripping means comprises a slit formed in said retaining means, said slit extending from top to bottom through said distal extension and from an end opposite said bite portion up to said bite portion to selectively retain said film packet in said slit in a plurality of positions of adjustment vertically relative to said extension both above and below said extension.

4. The retaining device of claim 1 where said arcuate tip locator is substantially parallel to a plane substantially perpendicular to said edge, said locator extending both above and below said arm.

5. The retaining device of claim 1 which further comprises a substantially straight handle integral and substantially co-planar with said bite portion, said retaining means and said arm, said handle extending substantially parallel to said slit.

6. The retaining device of claim 1 wherein said slit is shaped and positioned to hold said film packet in a plane substantially transverse to said bite portion.

* * * * *